(12) United States Patent
Alberto et al.

(10) Patent No.: US 6,344,178 B1
(45) Date of Patent: Feb. 5, 2002

(54) METHOD FOR THE PREPARATION OF FACIAL METAL TRICARBONYL COMPOUNDS AND THEIR USE IN THE LABELLING OF BIOLOGICALLY ACTIVE SUBSTRATES

(75) Inventors: Roger Alberto, Winterthur; Roger Schibli, Leibstadt; André Egli, Stäfa, all of (CH)

(73) Assignee: Mallinckrodt Inc., St. Louis, MO (US)

( * ) Notice: Subject to any disclaimer, the term of this patent is extended or adjusted under 35 U.S.C. 154(b) by 0 days.

(21) Appl. No.: 09/403,704

(22) PCT Filed: Apr. 21, 1998

(86) PCT No.: PCT/US98/07979

§ 371 Date: Oct. 22, 1999

§ 102(e) Date: Oct. 22, 1999

(87) PCT Pub. No.: WO98/48848

PCT Pub. Date: Nov. 5, 1998

(30) Foreign Application Priority Data

Apr. 25, 1997 (EP) ............................................ 97201232

(51) Int. Cl.$^7$ ........................... A61K 49/00; C07F 5/00; A61B 5/055

(52) U.S. Cl. .......................... 424/1.65; 534/10; 534/14; 424/9.36

(58) Field of Search ................................ 424/1.65, 1.69, 424/1.73, 1.61, 1.49, 1.53, 9.3, 9.36, 9.361, 1.17; 534/10, 14, 15; 556/45; 987/19; 206/223, 569, 570

(56) References Cited

U.S. PATENT DOCUMENTS 4,935,222 A * 6/1990 Deutsch et al. ............ 424/1.11

OTHER PUBLICATIONS

Beck, W. et al., Mitallkomplexe mit biologisch wichtigen liganded, Jour. of Organometallic Chemistry, 191, pp. 73–77, 1980.*

Alberto, R. et al., Metal carbonyl synethesis XXII, Journal of Organometallic Chemistry, 493, pp. 119–127, 1995.*

* cited by examiner

*Primary Examiner*—Michael G. Hartley

(57) ABSTRACT

The invention relates to a method of preparing facial metal tricarbonyl compounds and further coordinated facial metal tricarbonyl compounds in water or an aqueous medium. The invention further relates to the use of said facial metal tricarbonyl compounds in the labelling of biologically active substrates and other ligands, and to a kit for preparing a facial metal tricarbonyl compound or further coordinated facial metal tricarbonyl compounds.

17 Claims, 1 Drawing Sheet

METHOD FOR THE PREPARATION OF FACIAL METAL TRICARBONYL COMPOUNDS AND THEIR USE IN THE LABELLING OF BIOLOGICALLY ACTIVE SUBSTRATES

This application is a 371 of PCT/US98/07979, filed Apr. 21, 1998.

The invention relates to a method of preparation of facial metal tricarbonyl compounds and further co-ordinated facial metal tricarbonyl compounds. The invention further relates to the use of said facial metal tricarbonyl compounds in the labelling of biologically active substrates and other ligands, and to a kit for preparing a facial metal tricarbonyl compound or further co-ordinated facial metal tricarbonyl compounds.

The application of metal complexes, with a wide variety of radionuclides, in the field of nuclear medicine has become a major tool in diagnosis and also more recently in therapy. The metal complexes are often attached to a biologically active substrate that acts as a targeting agent. One of the most widely applied procedures for the metal-labelling of biologically active substrates such as proteins, peptides, sugars or small biologically active compounds consists in stabilizing the M(V)=O moiety of (radioactive) metals of group 7B of the periodic table with different tetradentate ligands. After reduction, the M(V)=O moiety is intermediately stabilized with a larger amount of an auxiliary ligand such as glucoheptonate which is subsequently substituted by the chelator attached to the system to be labelled. This method has proven to be successful in many cases but suffers from some major disadvantages such as the required high denticity and the bulkiness of the ligand and the difficulty in synthesizing and attaching such ligand.

It is known in the art (Alberto et al., J. Nucl. Biol. and Med. 1994, 38, 388–90) that facial metal tricarbonyl complexes of radioactive metals of group 7B of the periodic table are very convenient starting materials for substitution reactions in organic solvents as well as in water, as these compounds are stable in water for weeks, even if exposed to air. Therefore said compounds would be very useful for the labelling of biologically active substrates, such as amino acids, peptides, proteins, sugars and any receptor binding molecules. A major drawback, however, of these compounds until now is that they have only been available from high temperature carbonylation reactions and with the aid of the pyrophoric and toxic and therefore dangerous reducing agent $BH_3$ (Alberto et al., Low CO pressure synthesis of $(NEt)_2[MX_3(CO)_3]$ (M=Tc, Re) and its Substitution Behaviour in Water and Organic Solvents. Technetium in Chemistry and Nuclear Medicine, No 4, Cortina International, Milano, 1994).

It is the objective of the present invention to provide for a method of preparing facial metal tricarbonyl compounds of (radioactive) metals of group 7B with the aid of easily available and low-toxic starting materials at moderate temperature and at normal pressure of CO, in a reasonable time and with high yield. Such a method would be a powerful tool that can be used for the synthesis of diagnostic and therapeutic agents, especially for the synthesis of said diagnostic and therapeutic agents derived from radioactive metals with a short lifetime, in order to have access to these labelled compounds in poorly-equipped hospital laboratories. When the above mentioned diagnostic agent is labelled with a radionuclide it can be detected by the so-called single photon emission computerized tomography (SPECT and SPET), when it is labelled with a paramagnetic metal atom it can be detected by magnetic resonance imaging.

The above-defined objective can be achieved, according to the present invention, by a method of preparing a compound of the general formula $$\text{fac-}[M(CO)_3(OH_2)_3]^+ \tag{I}$$

wherein M is Mn, $^{99m}$Tc, $^{186}$Re or $^{188}$Re,
by reacting a metal in the permetallate form ($MO_4^-$ form) with carbon monoxide and a reducing agent, characterized in that a mixture of a base, a reducing agent soluble in water but not substantially decomposed by water, and optionally a stabilizing agent is solved in a water containing solvent system containing a solution of the metal in the permanganate, pertechnetate or perrhenate form in the presence of carbon monoxide. The metal M is preferably $^{99m}$Tc, $^{186}$Re or $^{188}$Re, as these radionuclides, when used in diagnostic or therapeutic agents, have the advantage that they can be applied in very low concentrations, which minimizes the risk of toxicity.

The term "not substantially decomposed by water" means that upon the addition of the solution of permanganate, pertechnetate or perrhenate in water, the velocity of the decomposition reaction of the reducing agent with water is zero or very low compared with the reaction of said reducing agent with the permanganate, pertechnetate or perrhenate, so that the reaction with said permetallate is completed when still enough of the reducing agent is present. It is very surprising that a quantitative reduction of permetallates in water containing solvent systems can be achieved at moderate temperature and in reasonable times with reducing agents that are nucleophilic and that are generally considered as less reactive than the electrophilic reducing agent $BH_3$ known in the art.

The method of the invention can be easily performed just by mixing the permetallate solution with the other reagents in the presence of carbon monoxide. The permetallate solution may optionally contain halide ions needed for the elution of the permetallate from a generator. The carbon monoxide may be supplied by using a closed system with an atmosphere containing a sufficient amount of carbon monoxide, or by flushing the carbon monoxide gas through the solution. The base used is preferably an inorganic base, selected from the group of stable hydroxides and carbonate salts such as NaOH, KOH, $NaHCO_3$, $Na_2CO_3$, $KHCO_3$, $K_2CO_3$, $Ca(OH)_2$ and $Mg(OH)_2$. Most preferred is $Na_2CO_3$. The base is added in a molar ratio to the reducing agent of between 0.1 and 2, and preferably in a molar ratio of approx. 0.35. The reaction can be performed with and without a stabilizing agent. As a stabilizing agent gentisate (2,5-dihydroxybenzoate), glucoheptonate, citrate or tartrate can be used. The preferred stabilizing agent is tartrate, e.g. as NaK-tartrate. The stabilizing agent is added to the reaction mixture in such an amount that its concentration is higher than that of the metal to be reduced. For the reduction several reducing agents can be used, such as borohydride anion ($BH_4^-$) or substituted borohydride anion wherein up to three of the hydrogen atoms which comprise the borohydride anion have been independently replaced by inert substituents. Examples of said inert substituents are alkoxy or alkylcarbonyloxy groups containing 1 to 10 carbon atoms and cyano groups. The counterion of the reducing group may consist of a metal of group 1A or 2A of the periodic table or zinc or an ammonium or tetrasubstituted ammonium or tetrasubstituted phosphonium ion, wherein the four substituents are each independently alkyl groups containing from 1 to 10 carbon atoms, hydroxyalkyl groups or alkoxyalkyl groups containing from 2 to 10 carbon atoms or aryl groups.

Preferred reduction reagent is borohydride anion, especially in the form of compounds such as sodium borohydride, potassium borohydride, lithium borohydride and zinc borohydride. Most preferred reducing agent is sodium borohydride. The reducing agent is reacted with the permetallate in a molar ratio higher than 3. The reduction reaction can be performed at a temperature between 20° C. and 100° C. The preferred reaction temperature is approx. 75° C. The heating of the reaction mixture can be performed in the normal way but also by micro-wave heating. The reaction can also be performed by the application of ultra sound, e.g. by carrying out the reactions in an ultrasonic bath at room temperature, normally leading to the same reaction rate at lower reaction temperature.

The compound of the general formula (I) obtained is very suitable for the labeling of biologically active substrates, such as amino acids, peptides, proteins, sugars, small receptor binding molecules or cells. Examples of peptides that may be labelled are growth factors, somatostatin, bombesin, insulin, LHRH, gastrin, gastrin releasing peptide, thyrotropin releasing hormone, thyroid stimulating hormone, prolactin, vasoactive intestinal peptide (VIP), pituitary adenylate cyclase-activating polypeptide (PACAP), angiotensin, neurotensin, interferons, IL-1, IL-4 and IL-6, monoclonal antibodies and their analogues and derivatives. After labelling with a suitable labelling substance these peptides can e.g. be used in the detection and localisation or treatment of malignant human tumours.

Examples of sugars that may be labelled are glucose and deoxyglucose and derivatives of said compounds.

Small receptor binding molecules are defined as non-peptide molecules which are binding to a receptor and normally have a molecular mass below approximately 500 Daltons. Examples of small receptor binding molecules that may be labelled are substances for the serotonergic system as described in WO 96/30054, or substances for the dopaminergic system (e.g. raclopride, β-CIT, lisuride), for the cholinergic system (e.g. epibatidine), for the glutaminergic system (e.g. mematine) or for the benzodiazepine system (e.g. flumazenil, iomazenil). Examples of metabolic active molecules that may be labelled are DOPA, Tyrosine, mIBG, MAO-I and analogues thereof.

Examples of cells that may be labelled are red and white blood cells.

As a result of the labeling of (biologically active) substrates with a compound of the general formula I, a further coordinated compound of the general formula

  (II),

  (III)

or

  (IV), wherein:

M is Mn, $^{99m}$Tc, $^{186}$Re or $^{188}$Re;

$L_1$ is a monodentate ligand, $L_2$ is selected from the group consisting of a bidentate ligand and two monodentate ligands, and $L_3$ is selected from the group consisting of a tridentate ligand, a monodentate ligand and a bidentate ligand, and three monodentate ligands;

X is $H_2O$ or a halide ion;

n the sum of the charge of the ligands $L_1$ or $L_2$ or $L_3$ and X increased with one + charge is obtained.

After the labeling reaction the ligand X is usually $H_2O$. One of the $H_2O$ ligands may, however, be replaced by a halide ion, when available, to neutralize the charge of the complex. This is often the case for compounds of the general formula Ill. When the ligand $L_1$, $L_2$ or $L_3$ before and/or after labeling with the facial metal tricarbonyl compound is the biologically active molecule, the present invention gives easy access to compounds that directly can be used as a diagnostic and therapeutic agent.

Examples of monodentate ligands within the definition of $L_1$, $L_2$ and $L_3$ are (biologically active) substrates bearing groups such as phosphines, isonitriles, nitrites, imidazoles, thioethers and pyridine-like aromatic amines. Examples of bidentate ligands within the definition of $L_2$ and $L_3$ are (biologically active) substrates bearing pyridin, imidazole or pyrazole groups, such as histidine, histamine, functionalized imidazole systems, bidentate thioethers, bidentate isocyanides, Schiff-base type ligands and picolinic acid.

Examples of tridentate ligands within the definition of $L_3$ are tris-pyrazolyl borate, tris-pyrazolylmethane, tris-imidazolyl borate, tris-pyrazolylmethane, 1,4,7-trithiacyclononane (9-ane$S_3$) and triazacyclononane (9-ane$N_3$), histidine, methionine, cystein derivatized at the thiol group to give a thioether and cyclopentadienyl derivatives.

In some cases it may be advantageous to prepare the radiolabelled bioactive compound in one step. This objective can be achieved according to the present invention, with a method of preparing a compound of the general formula

  (II),

  (III)

or

  (IV), wherein:

M is Mn, $^{99m}$Tc $^{186}$Re or $^{188}$Re;

$L_1$ is a monodentate ligand, $L_2$ is selected from the group consisting of a bidentate ligand and two monodentate ligands, and $L_3$ is selected from the group consisting of a tridentate ligand, a monodentate ligand and a bidentate ligand, and three monodentate ligands;

X is $H_2O$ or a halide ion;

n the sum of the charge of the ligands $L_1$ or $L_2$ or $L_3$ and X increased with one + charge;

characterized in that a mixture of a base, ligands $L_1$ or $L_2$ or $L_3$, a reducing agent soluble in water but not substantially decomposed by water, and optionally a stabilizing agent is solved in a water containing solvent system containing a solution of the metal in the permanganate, pertechnetate or perrhenate form in the presence of carbon monoxide and optionally in the presence of halide.

Especially in the case of radiolabelled compounds it is frequently impossible to put the ready-for-use composition at the disposal of the user, in connection with the often poor shelf life of the radiolabelled compound and/or the short half-life of the radionuclide used. In such cases the user will carry out the labelling reaction with the metal in the clinical hospital or laboratory. For this purpose the various reaction ingredients are then offered to the user in the form of a so-called "kit". It will be obvious that the manipulations necessary to perform the desired reaction should be as simple as possible to enable the user to prepare from the kit the radioactive labelled composition by using the facilities that are at his disposal. Therefore the invention also relates to a kit for preparing a labelling composition, which labelling composition contains compound of formula I as the labelling agent. Such a kit for the labelling of a biologically active substrate, according to the present invention, comprises (i) a reducing agent soluble in water but not substantially decomposed by water, (ii) a base, (iii) if desired, a stabilizing agent and/or a chelator and (iv) if desired one or more inert pharmaceutically acceptable carriers and/or formulating agents and/or adjuvants, at least one of said ingredients (i) to (iv) being stored in a container having an atmosphere containing a sufficient amount of carbon monoxide, said ingredients (i) to (iv) optionally independently being combined, and (v) instructions for use with a prescription for reacting the ingredients of the kit with a metal selected from the group consisting of Mn, $^{99m}$Tc, $^{186}$Re or $^{188}$Re in the form of a permetallate solution.

It is the merit of the present invention, disclosing an easy way of preparing facial tricarbonyl metal compounds within a time-frame that is reasonable compared with the half-life time of the radioactive isotopes involved, and with high yields, that a kit can be prepared for the labelling of biologically active substrates with said facial tricarbonyl metal compounds.

In some cases it may be advantageous to enclose a bioactive substrate in the kit so that a kit is obtained for the preparation of a radiopharmaceutical composition.

Alternatively the biologically active compound is formed upon the reaction of the ligand with the facial metal tricarbonyl compound. Such a kit for the preparation of a diagnostic and therapeutic pharmaceutical composition, according to a different embodiment of the present invention, comprises (i) a suitable substrate to be labelled with a metal selected from the group consisting of Mn, $^{99m}$Tc, $^{186}$Re or $^{188}$Re, (ii) a reducing agent soluble in water but not substantially decomposed by water, (iii) a base, (iv) if desired, a stabilizing agent and/or a chelator, (v) if desired one or more inert pharmaceutically acceptable carriers and/or formulating agents and/or adjuvants, at least one of said ingredients (i) to (v) being stored in a container having an atmosphere containing a sufficient amount of carbon monoxide, said ingredients (i) to (v) optionally independently being combined, and (vi) instructions for use with a prescription for reacting the ingredients of the kit with said metal in the form of a permetallate solution.

The preparation of the diagnostic and therapeutic pharmaceutical composition with the aid of the above mentioned kit enclosing a (biologically active) substrate can take place in two alternative embodiments. In the first embodiment the facial tricarbonyl metal compound is prepared first and then reacted with the substrate to be labelled. In the second embodiment the reduction step is carried out in the presence of the substrate to be labelled, directly leading to the labelled compound.

Figure 1:
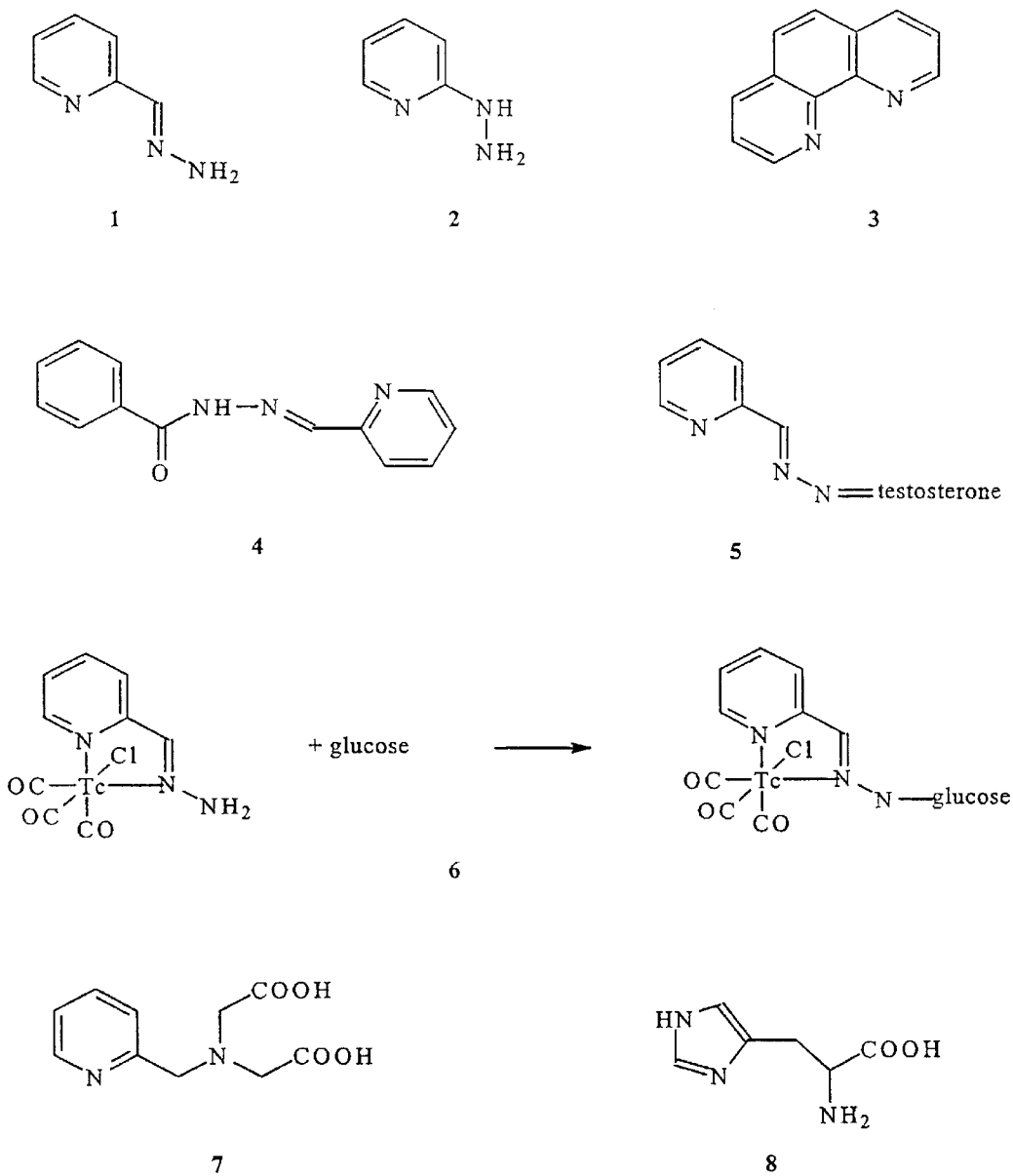
FIG. 1 Overview of ligands for the preparation of complexes of composition [$^{99m}$TcL(CO)$_3$] as described in Example 2.

The invention will now be described in greater detail with reference to the following specific Examples.

EXAMPLE 1

Synthesis of [$^{99m}$Tc(OH$_2$)$_3$(CO)$_3$]$^+$ from Aqueous Solution

In a 10 ml closable vial the following chemicals are put together: 5.5 mg of NaBH$_4$, 4.0 mg Na$_2$CO$_3$ and 20.0 mg NaKtartrate. The vial is closed with a serum stopper and flushed for 10 minutes with carbon monoxide gas with the aid of a syringe. 3 ml of a 0.9% NaCl solution from a Mo-99/Tc-99m generator, having an activity of about 100 mCi, is added via the septum and the vial is heated to 75° C. during 30 minutes and then cooled to room temperature. The product is analysed by TLC on standard Merck silica gel plates with methanol/conc. HCl=99/1 as mobile phase followed by analysis of the silica gel plate by means of a radioactivity scanner. The yield of the reduction of pertechnetate to facial [$^{99m}$Tc(OH$_2$)$_3$(CO)$_3$]$^+$ is >95% according to TLC. After neutralizing the solution with a solution of PBS (phosphate buffer (pH=7.4, saline 0.9%)) a neutral physiological solution, suitable for labelling is obtained. Table 1 shows that solutions of [$^{99m}$Tc(OH$_2$)$_3$(CO)$_3$]$^+$ having an activity up to 700 mCi can be obtained under different reaction conditions.

TABLE 1

Preparation of [$^{99m}$Tc(OH$_2$)$_3$(CO)$_3$]$^+$ under different reaction conditions.

| Exp. | Stabilizing agent | Volume TcO$_4^-$ sol. (ml) | Activity (mCi) | Solvent | Temp. (° C.) | React. time (min) | Yield (TLC) (%) |
|---|---|---|---|---|---|---|---|
| 1 | NaK tartrate | 3 | ≈100 | H$_2$O | 75 | 30 | >95 |
| 2 | NaK tartrate | 3 | ≈400 | H$_2$O | 75 | 30 | >95 |
| 3 | NaK tartrate | 3 | ≈700** | H$_2$O | 75 | 30 | >95 |
| 4 | NaK tartrate | 3 | n.d.* | H$_2$O | 75 | 30 | >95 |
| 5 | NaK tartrate | 6 | n.d.* | H$_2$O | 75 | 30 | >95 |
| 6*** | NaK tartrate | 3 | n.d.* | H$_2$O | 75 | 30 | 40 |
| 7 | — | 3 | n.d.* | H$_2$O | 75 | 30 | 70 |
| 8 | Na citrate | 3 | n.d.* | H$_2$O | 75 | 30 | 20 |
| 9 | Na formiate | 3 | n.d.* | H$_2$O | 75 | 30 | 35 |
| 10 | NaK tartrate | 3 | n.d.* | H$_2$O/EtOH 80/20 | 75 | 30 | >95 |
| 11 | NaK tartrate | 3 | n.d.* | H$_2$O | 100 | 10 | 80 |

*Activity not determined exactly, but always between 50 and 200 mCi.
**Activity determined after dilution to 1%
***4.0 mg Ca(OH)$_2$ has been used as a base instead of 4.0 mg Na$_2$CO$_3$

EXAMPLE 2

Synthesis of Complexes of Composition [$^{99m}$TcL(CO)$_3$]

2.1 Synthesis of [$^{99m}$Tc(his)(CO)$_3$] via [$^{99m}$Tc(OH$_2$)$_3$(CO)$_3$]$^+$ After completion of the reaction as described in Example 1, 0.1 μmol of histidine is added to the solution of pH 7.4. According to TLC the reaction is complete after 1 hour. When 0.01 μmol of histidine is added at room temperature, the reaction takes 5–10 hours before completion; the reaction is completed in less than 1 hour at 70° C.

2.2 Direct Synthesis of [$^{99m}$Tc(his)(CO)$_3$]

The experiment is carried out as described in Example 1. Concerted to the addition of the generator eluate to the cold vial, 0.03 μmol of histidine is added to said cold vial. After heating during 30 minutes [$^{99m}$Tc(his)(CO)$_3$]$^+$ is obtained in almost quantitative yield according to TLC.

2.3 Synthesis of [$^{99m}$Tc((lys-gly-(his)$_5$)(CO)$_3$]$^+$ via [$^{99m}$Tc(OH$_2$)$_3$(CO)$_3$]$^+$ After completion of the reaction as described in Example 1, 500 pmol of the octapeptide lys-gly-gly-(his)$_5$ is added to the solution. According to TLC the reaction is complete after 1 hour at room temperature. When 300 pmol of lys-gly-gly-(his)$_5$ is added the reaction takes 3 hours to complete.

2.4 Summary of Preparation of Further Complexes of Composition [$^{99m}$TcL(CO)$_3$]

The [$^{99m}$Tc(OH$_2$)$_3$(CO)$_3$]$^+$ is prepared as described in Example 1 and neutralized. The ligand (see FIG. 1) is added with subsequent complexation time and temperature and in amount and concentration as indicated in Table 2. Table 2 also indicates the yields obtained as determined by TLC analysis as described in Example 1 and the possibility of carrying out the reaction in a one pot process.

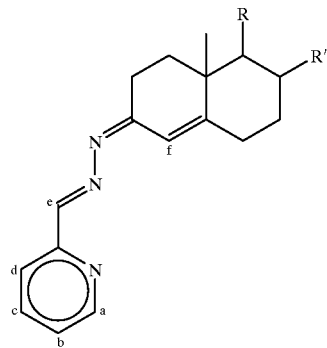

EXAMPLE 3

Labelling of Antibodies with [$^{99m}$Tc(OH$_2$)$_3$(CO)$_3$]$^+$

3.1 Labelling as Function of Concentration

Labelling kinetics is tested as a function of Mab concentration. Concentration above 2–3 mg/ml yields quantitative labelling after 2 hours, whereas below 1 mg the yield is about 40–50% according to TLC.

3.2. In vitro Biological Activity of Labelled Monoclonal Antibody 35 (Mab-35)

An amount of [$^{99m}$Tc(OH$_2$)(CO)$_3$]$^+$ as prepared in Example 1 is used for labelling of 1.2 mg of Mab-35. After 3 hours of incubation at 37° C., the Mab is separated over a PD-10 size exclusion gel chromatography column with 38% yield. The labelled Mab is brought to a Lindmo testing (T. Lindmo, P. A. Brunn, Methods in Enzymology 1986, 121, 678), showing 100% biological activity.

TABLE 2

Preparation of [$^{99m}$TcL(CO)$_3$] with different ligands and under different reaction conditions.

| Ligand (FIG. 1) | pH. | time | temp | Conc. | absolute amount | yield | one pot**** |
|---|---|---|---|---|---|---|---|
| 1 | PBS | 30' | 70° C. | 3 μM | 5 nmol | 92% | partially |
| 2 | PBS | 2–3 h | 37° C. | 20 μM | 10 nmol | 74% | yes |
| 3 | PBS | 4 h | 37° C. | 100 μM | 50 nmol | 89% | yes |
| 4 | PBS | 6 h | 37° C. | 100 μM | 50 nmol | 72% | — |
| 5 | PBS/CH$_3$OH | 1 h | 50° C. | 100 μM | 100 nmol | 65% | — |
| 6 | PBS | 1 h + 1 h | 50° C. | * | | 97% + 30% | — |
| 7*** | PBS | 30' | 75° C. | 25 μM | 25 nmol | 95% | yes |
| 7*** | PBS | 15' | ** | 25 μM | 25 nmol | 95% | yes |
| 8 | PBS | 1 h | 75° C. | 10 μM | 2 nmol | 95% | yes |

*50 μl 10$^{-3}$M ligand 1, then 50 μl 10$^{-2}$M glucose
**15 min ultra sound r.t.
***After the reaction the product was stored for 23 h at 37° C. and appeared to be stable
****possiblity to perform as a one pot synthesis From the compound derived from ligand 5 (see structure below) the $^1$H-NMR spectrum was determined before and after complexation with "cold" [Tc(OH$_2$)$_3$(CO)$_3$]$^+$. A: aromatic region of NMR spectrum before complexation: $^1$H-NMR (CDCl$_3$)[r.t., δ in ppm]=8.75 (1H, d)(a), 8.36 (1H, s)(e), 8.14 (1H, d)(d), 7.99 (1H, t)(b), 7.55 (1H, m)(c), 6.07 (1H, s)(f). B: aromatic region of NMR spectrum after complexation: $^1$H-NMR (CDCl$_3$)[r.t., δ in ppm]=9.12 (1H, d)(a), 8.51 (1H, s)(e), 8.37 (1H, t)(b), 8.19 (1H, d)(d), 7.87 (1H, m)(c), 6237 (1H, s)(f).

EXAMPLE 4

Labelling of His-Neurotensin(8-13) with [$^{99m}$Tc(OH$_2$)$_3$(CO)$_3$]$^+$ 0.9 ml of [$^{99m}$Tc(OH$_2$)$_3$(CO)$_3$]$^+$ as prepared in example 1 is mixed with 0.1 ml of 10$^{-3}$M His-Neurotensin(8-13) (HRRPYIIL) and kept in a sealed tube at 75° C. for one hour. After this time the reaction mixture is cooled to room temperature. As evident from reversed phase column HPLC the yield is >95%. The K$_d$ of this compound on coloncarcinoma cells HT29 is 1.0 nM.

EXAMPLE 5

Labelling of the Protein Fragment Recombinant scFv with 6xHis-tag with $[^{99m}Tc(OH_2)_3(CO)_3]^+$ 0.1 ml of $[^{99m}Tc(OH_2)_3(CO)_3]^+$ as prepared in Example 1 is mixed with 0.1 ml of 1M MES-buffer pH 6.2 and 0.1 ml of 150 µM scFv-6xHis and kept at 37° C. for 20 min. After this time the reaction mixture is separated on a Sephadex® G-25 Superfine sizing column. Typical incorporations of $^{99m}Tc$ are 70% to 84%, with biological activities (measured by the Lindmo testing mentioned in Example 3) ranging from 57% to 90%. $K_d$ values were not significantly altered by the $^{99m}Tc$ incorporation: measurement by BIAcore of the unlabeled scFv: $0.5 \times 10^{-8}$M, $^{99m}Tc$-labelled scFv: $1 \times 10^{-8}$M, $^{125}I$-labelled scFv: $4 \times 10^{-8}$M.

EXAMPLE 6

Labelling of Biotin with $[^{99m}Tc(OH_2)_3(CO)_3]^+$ $[^{99m}Tc(OH_2)_3(CO)_3]^+$ is prepared as described in example 1. 1.300 µl of a $10^{-3}$M biotin-hydrazide-pyridine solution is added to 2 ml of the Tc-carbonyl compound and is incubated at 50° C. for 2 hours to yield a Tc labelled compound with a purity of 50%. The compound is purified over an equilibrated (5 ml MeOH/H$_2$O=1/1) SepPac column by loading and eluting by-products with 2 ml H$_2$O and then with 4 ml MeOH/H$_2$O=1/1 followed by eluting the desired product with 2 ml of MeOH. Final purity of the compound is 98%. Stability control: No decomposition in methanol after 24 hours; 32% decomposition in PBS buffer after 24 hours. Results of binding test to Streptavidin-beads: 0.5% unspecific binding and 81% specific binding.

What is claimed is:

1. Method of preparing a compound of the general formula $$\text{fac-}[M(CO)_3(OH_2)_3]^+ \qquad (I)$$

wherein M is Mn, $^{99m}Tc$, $^{186}Re$ or $^{188}Re$, by reacting a metal in the permetallate form with carbon monoxide and a reducing agent, characterized in that a mixture of a base, a reducing agent soluble in water but not substantially decomposed by water, and optionally a stabilizing agent is solved in a water containing solvent system containing a solution of the metal in the permanganate, pertechnetate or perrhenate form in the presence of carbon monoxide.

2. Method of preparing a compound of the general formula $$\text{fac-}[M(CO)_3(X)_2L_1]^n \qquad (II),$$

$$\text{fac-}[M(CO)_3(X)L_1]^n \qquad (III)$$

or $$\text{fac-}[M(CO)_3L_3]^n \qquad (IV),$$

wherein:

M is Mn, $^{99m}Tc$, $^{186}Re$ or $^{188}Re$;

$L_1$ is a monodentate ligand, $L_2$ is selected from the group consisting of a bidentate ligand and two monodentate ligands, and $L_3$ is selected from the group consisting of a tridentate ligand, a monodentate ligand and a bidentate ligand, and three monodentate ligands;

X is H$_2$O or a halide ion;

n is the sum of the charge of the ligands $L_1$ or $L_2$ or $L_3$ and X increased with one + charge;

characterized in that a compound of the general formula $$\text{fac-}[M(CO)_3(OH_2)_3]^+ \qquad (I)$$

prepared by reacting a metal in the permetallate form with carbon monoxide and a reducing agent, wherein a mixture of a base, a reducing agent soluble in water but not substantially decomposed by water, and optionally a stabilizing agent is solved in a water containing solvent system containing a solution of the metal in the permanganate, pertechnetate or perrhenate form in the presence of carbon monoxide, is reacted with ligands $L_1$, $L_2$ or $L_3$, optionally in the presence of a halide.

3. Method of preparing a compound of the general formula $$\text{fac-}[M(CO)_3(X)_2L_1]^n \qquad (II),$$

$$\text{fac-}[M(CO)_3(X)L_2]^n \qquad (III)$$

or $$\text{fac-}[M(CO)_3L_3]^n \qquad (IV),$$

wherein:

M is Mn, $^{99m}Tc$, $^{186}Re$ or $^{188}Re$;

$L_1$ is a monodentate ligand, $L_2$ is selected from the group consisting of a bidentate ligand and two monodentate ligands, and $L_3$ is selected from the group consisting of a tridentate ligand, a monodentate ligand and a bidentate ligand, and three monodentate ligands;

X is H$_2$O or a halide ion;

n is the sum of the charge of the ligands $L_1$ or $L_2$ or $L_3$ and X increased with one + charge;

characterized in that a mixture of a base, ligands $L_1$ or $L_2$ or $L_3$, a reducing agent soluble in water but not substantially decomposed by water, and optionally a stabilizing agent is dissolved in a water containing solvent system containing a solution of the metal in the permanganate, pertechnetate or perrhenate form in the presence of carbon monoxide and optionally in the presence of a halide.

4. Method according to claim 2 or 3, characterized in that the ligands $L_1$–$L_3$ are derived from biologically active substrates selected from the group consisting of amino acids, peptides, proteins, sugars, small receptor binding molecules and body cells.

5. Method according to claim 4, characterized in that the substrate is an amino acid, a peptide or a protein.

6. Method according to claim 1 or 3, characterized in that the base is an inorganic base.

7. Method according to claim 1 or 3, characterized in that the molar ratio between the base and the reducing agent is between 0.1 and 2.

8. Method according to claim 1 or 3, characterized in that the reducing agent is selected from the group consisting of borohydride anion and substituted borohydride anion wherein up to three of the hydrogen atoms which comprise the borohydride anion have been replaced by inert substituents.

9. Method according to claim 8, characterized in that the reducing agent is a borohydride anion derived from of a salt selected from the group consisting of sodium borohydride, potassium borohydride, lithium borohydride and zinc borohydride.

10. Method according to claim 9, characterized in that the reducing agent is sodium borohydride.

11. Method according to claim 10, characterized in that the molar ratio of the reducing agent to the permetallate is at least 3.

12. Method according to claim 1 or 3, characterized in that the reaction temperature is between 20° C. and 100° C.

13. A kit for the preparation of labelling composition, comprising (i) a reducing agent soluble in water but not substantially decomposed by water, (ii) a base, (iii) if desired, a stabilizing agent and/or chelator and (iv) if desired one or more inert pharmaceutically acceptable carriers and/or formulating agents and/or adjuvants, at least one of said ingredients (i) to (iv) being stored in a container having an atmosphere containing a sufficient amount of carbon monoxide to form a complex of a formula $M(CO)_3$, said ingredients (i) to (iv) optionally independently being combined, and (v) instructions for use with a prescription for reacting the ingredients of the kit with a metal selected from the group consisting of Mn, $^{99m}$Tc, $^{186}$Re or $^{188}$Re in the form of a permetallate solution.

14. A kit for the preparation of a diagnostic pharmaceutical composition, comprising (i) a substrate to be labelled with a metal selected from the group consisting of Mn, $^{99m}$Tc, $^{186}$Re or $^{188}$Re, (ii) a reducing agent soluble in water but not substantially decomposed by water, (iii) a base, (iv) if desired, a stabilizing agent and/or chelator, (v) if desired one or more inert pharmaceutically acceptable carriers and/or formulating agents and/or adjuvants, at least one of said ingredients (i) to (v) being stored in a container having an atmosphere containing a sufficient amount of carbon monoxide to form a complex of a formula $M(CO)_3$, said ingredients (i) to (v) optionally independently being combined, and (vi) instructions for use with a prescription for reacting the ingredients of the kit with a metal in the form of a permetallate solution.

15. Method according to claim 1 or 3, characterized in that the base is an inorganic base selected from the group consisting of NaOH, KOH, $NaHCO_3$, $Na_2CO_3$, $KHCO_3$, $K_2CO_3$, $Ca(OH)_2$ and $Mg(OH)_2$.

16. Method according to claim 7, characterized in that the molar ratio between the base and the reducing agent is approximately 0.35.

17. Method according to claim 12, characterized in that the reaction temperature is approximately 75° C.

* * * * *